US009376417B2

(12) United States Patent
Himmler et al.

(10) Patent No.: US 9,376,417 B2
(45) Date of Patent: Jun. 28, 2016

(54) PROCESS FOR PREPARING ARYL- AND HETEROARYLACETIC ACID DERIVATIVES

(71) Applicant: BAYER INTELLECTUAL PROPERTY GMBH, Monheim (DE)

(72) Inventors: Thomas Himmler, Odenthal (DE); Lukas J. Goossen, Kaiserslautern (DE); Felix Rudolphi, Schriesheim (DE); Bingrui Song, Kaiserslautern (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/686,886

(22) Filed: Apr. 15, 2015

(65) Prior Publication Data

US 2015/0315171 A1 Nov. 5, 2015

Related U.S. Application Data

(63) Continuation of application No. 14/002,691, filed as application No. PCT/EP2012/053233 on Feb. 27, 2012, now Pat. No. 9,096,568.

(60) Provisional application No. 61/448,379, filed on Mar. 2, 2011.

(30) Foreign Application Priority Data

Mar. 2, 2011 (EP) ..................................... 11156559

(51) Int. Cl.
*C07D 333/24* (2006.01)
*C07C 67/343* (2006.01)
*C07C 319/20* (2006.01)
*C07C 253/30* (2006.01)
*C07C 201/12* (2006.01)

(52) U.S. Cl.
CPC ............ *C07D 333/24* (2013.01); *C07C 67/343* (2013.01); *C07C 201/12* (2013.01); *C07C 253/30* (2013.01); *C07C 319/20* (2013.01)

(58) Field of Classification Search
CPC .. C07C 67/343; C07C 319/20; C07C 201/12; C07C 253/30; C07C 205/56; C07C 255/57; C07C 323/52; C07C 323/62; C07C 69/612; C07C 69/616; C07C 69/65; C07C 69/734; C07C 69/738; C07C 69/76
See application file for complete search history.

(56) References Cited

U.S. PATENT DOCUMENTS

| | | | |
|---|---|---|---|
| 5,994,274 | A | 11/1999 | Fischer et al. |
| 6,251,830 | B1 | 6/2001 | Fischer et al. |
| 6,469,196 | B2 | 10/2002 | Fischer et al. |
| 6,759,548 | B2 | 7/2004 | Fischer et al. |
| 2002/0022575 | A1 | 2/2002 | Fischer et al. |
| 2003/0144504 | A1 | 7/2003 | Fischer et al. |
| 2005/0176987 | A1 | 8/2005 | Goossen |
| 2011/0098484 | A1 | 4/2011 | Saitoh et al. |

FOREIGN PATENT DOCUMENTS

| | | |
|---|---|---|
| CN | 101151257 A | 3/2008 |
| DE | 10111262 | 12/2002 |
| EP | 0835243 | 4/1998 |
| WO | 9702243 | 1/1997 |
| WO | 2009/121919 | 8/2009 |

OTHER PUBLICATIONS

Beare et al. (J. Org. Chem., vol. 67, No. 2, 2002; p. 541-555).*
Culkin et al. (Acc. Chem. Res. 2003, 36, 234-245).*
Djakovitch et al. (J. Organomet. Chem. 2000, 606, 101-107).*
Aramendia et al. (Tetrahedron Lett. 2002, 43, 2847-2849).*
Liu et al. (J. Iran. Chem. Res. 1 (2008) 51-56).*
F.A. Carey et al., "The conversion of functional groups by nucleophilic substitution," XP-002671765. English translation.
Masanori Kosugi et al., "Palladium-catalyzed Displacement of Aryl Halide by Tin Analogue of Reformatsky Reagent", The Chemical Society of Japan, Bulk Chem. Soc. Jpn., 58, 3383-3384 (1985).
Lukas J. Goossen, "Pd-catalyzed synthesis of arylacetic acid derivatives from boronic acids", Chemical Communications, 2001, 669-670, XP-001088567.
Yoshinori Kondo et al., "Palladium catalyzed arylation of malonate accompanying in situ dealkoxycarbonylation", Chemical Communications, 2001, 2704-2705, XP-002630825.
Takao Sakamoto et al., "Synthesis of Methyl 2-(Heteroaryl) Propano-Ates Via Palladium-Catalyzed Reaction", Heterocycles, vol. 36, No. 11, 1993, 2509-2512.
Harold E. Zaugg et al., "Naphthoquinone Antimalarials, XIV. 2-Hydroxy-3-aryl-1, 4-naphthoquinones", J. Amer. Chem. Soc., vol. 70, (1948), 3224-3228.
William W. Leake et al., "The Phenylation of Esters by Reaction with Bromobenzene and Sodium Amide", J. Amer. Chem. Soc., 1959, 81, 1627-1630.
M. F. Semmelhack et al., "Total Synthesis of the Cephalotaxus Alkaloids. A Problem in Nucleophilic Aromatic Substitution", J. Amer. Chem. Soc. , 97:9, 1975, 2507-2516.
S.G. Lias et al., "A Nickel Catalyst for the Arylation and Vinylation of Lithium Ester Enolates", J. Amer. Chem. Soc., 1977, 99 (14), 4833-4835.
Motoi Kawatsura et al., "Simple, Highly Active Palladium Catalysts for Ketone and Malonate Arylation: Dissecting the Importance of Chelation and Steric Hindrance", J. Amer. Chem. Soc., 1999, 121, 1473-1478.

(Continued)

*Primary Examiner* — Valerie Rodriguez-Garcia
(74) *Attorney, Agent, or Firm* — McBee Moore Woodward Vanik IP, LLC

(57) ABSTRACT

The invention relates to a process for preparing aryl- and heteroarylacetic acids and derivatives thereof by reaction of aryl or heteroaryl halides with malonic diesters in the presence of a palladium catalyst, of one or more bases and optionally of a phase transfer catalyst. This process enables the preparation of a multitude of functionalized aryl- and heteroarylacetic acids and derivatives thereof, especially also the preparation of arylacetic acids with sterically demanding substituents.

12 Claims, No Drawings

(56) References Cited

OTHER PUBLICATIONS

Milco Van Leeuwen et al., "A Study of the Ferrous Ion-initiated SRN1 Reactions of Halogenoarenes with tert-Butyl Acetate and N-Acylmorpholine Enolates", J. Chem. Soc. Perkin Trans., 1993, 2433-2440.

Carla Carfagna et al., "Palladium-Catalyzed Coupling Reactions of Aryl Triflates or Halides with Ketene Trimethylsilyl Acetals. A New Route to Alkyl 2-Arylalkanoates", J. Org. Chem. 1991, 56, 261-263.

Kazumi Okuro et al., "Copper-Catalyzed Reaction of Aryl Iodides with Active Methylene Compounds", J. Org. Chem. 1993, 58, 7606-7607.

Muriel Durandetti et al., "Nickel-Catalyzed Direct Electrochemical Cross-Coupling between Aryl Halides and Activated Alkyl Halides", J. Org. Chem. 1996, 61, 1748-1755.

J F Fauvarque et al., "Catalysis of the Arylation of the Reformatsky Reagent by Palladium or Nickel Complexes. Synthesis of Aryl Acid Esters", J. Org. Chem. 177 (1979) 273-281.

Jacques Chaussard et al., "Use of Sacrificial Anodes in Electrochemical Functionalization of Organic Halides", Synthesis, 1990, 369-381.

F. Orsini et al., "Pd (0)-Mediated Cross-Coupling of Reformatsky Reagents with Vinyl- and Aryl Triflates", Synthetic Communications, 17(12), 1987, 1389-1402.

Fabio Agnelli et al., "Synthesis of Arylacetates by the Palladium-Catalyzed Cross-Coupling of Aryl Bromides and Copper(II) Enolates", Tetrahedron Letters, 39, 1998, 8807-8810.

Jacob G. Zeevaart et al., "Palladium-catalysed arylation of acetoacetate esters to yield 2-arylacetic acid esters", Tetrahedron Letters 45 (2004) 4261-4264.

Ismail Ozdemir et al., "Synthesis of arylacetic acid derivatives from diethyl malonate using in situ formed palladium (1,3-dialkylimidazolidin-2-ylidene) catalysts", Tetrahedron Letters 45 (2004) 5823-5825.

Jacob G. Zeevaart et al., "Copper(I) iodide-catalysed arylation of acetoacetate to yield 2-arylacetic acid esters", Tetrahedron Letters 48 (2007) 3289-3293.

F.A. Carey et al., "Organische Chemie Ein weiterfuhrendes Lehrbuch", 1995, VCH Verlagsgesellschaft mbH, XP-002671765.

Claudio Giordano et al., "Synthesis of Anti-Inflammatory-Arylalkanoic Acids by 1,2-Aryl Shift", New Synthetic Methods (42), Angew Chem. Int. Ed Engl 23 (1984) 413-419, XP-002332663.

V. M. Naidan et al., "A New Method for the Production of Arylacetic Acids", Zhurnal Obshchei Khimii, 1964, vol. 34, No. 5, 1469-1473.

European Search Report for EP Application No. 11 15 6559 dated Mar. 31, 2011.

International Search Report for PCT/EP2012/053233 Mailed March 30, 2012.

Culkin et al., (Acc. Chem. Res. 2003, 36, 234-245).

of Aramendia et al. (Tetrahedron Lett. 2002, 43, 2847-2849).

* cited by examiner

PROCESS FOR PREPARING ARYL- AND HETEROARYLACETIC ACID DERIVATIVES

CROSS REFERENCE TO RELATED APPLICATIONS

This application is a continuation of U.S. application Ser. No. 14/002,691, filed Oct. 31, 2013, which is a §371 National Stage Application of PCT/EP2012/053233, filed Feb. 27, 2012, which claims priority to European Application No. 11156559.4, filed Mar. 2, 2011, and U.S. Provisional Application No. 61/448,379, filed Mar. 2, 2011, the contents of which are incorporated herein by reference in their entireties.

BACKGROUND OF THE INVENTION

1. Field of the Invention

The invention relates to a process for preparing aryl- and heteroarylacetic acids and derivatives thereof by reaction of aryl or heteroaryl halides with malonic diesters in the presence of a palladium catalyst, of one or more bases and optionally of a phase transfer catalyst. This process enables the preparation of a multitude of functionalized aryl- and heteroarylacetic acids and derivatives thereof, especially also the preparation of arylacetic acids with sterically demanding substituents.

2. Description of Related Art

Typically, phenylacetic acid derivatives are prepared in multistage syntheses, most of which have low group tolerance. The preparation can be effected, for example, proceeding from acetophenones by a Willgerodt-Kindler reaction (see, for example, H. E. Zaugg et al., *J. Amer. Chem. Soc.* 70 (1948) 3224-8). In this method, however, large amounts of sulphur-containing wastes arise. Moreover, volatile sulphur compounds with a high level of odour nuisance can occur.

A further method for preparing arylacetic acids proceeds from benzyl bromides or chlorides. Sodium cyanide, for example, is used to prepare the corresponding nitrites therefrom, and these are subsequently hydrolysed. The benzyl bromides or chlorides required can be obtained, for example, by bromo- or chloromethylation of the corresponding aromatics. However, a disadvantage here is that the occurrence of highly carcinogenic compounds such as bis(chloromethyl) ether or bis(bromomethyl) ether cannot be ruled out, and so a high degree of safety measures has to be implemented in industry. Moreover, the halomethylation of substituted aromatics in many cases leads to isomer mixtures.

The carbonylation of benzyl halides in the presence of alcohols likewise gives phenylacetic esters. The already mentioned limited availability of benzyl halides and the need to use toxic CO gas, in some cases even under elevated pressure, are further disadvantages of this process.

There has also already been a disclosure of ketalizing a-chloroacetophenones and then subjecting the ketals to a rearrangement reaction (C. Giordano et al., *Angew. Chem.* 96 (1984) 413-9). The a-chloroacetophenones are obtained either by chlorination of acetophenones or directly by a Friedel-Crafts acylation of the aromatic in question with chloroacetyl chloride. This again gives rise to the disadvantage that the Friedel-Crafts acylations of substituted aromatics frequently proceed unselectively.

A further known method for preparing phenylacetic acids consists in diazotizing a corresponding aniline in the first step, reacting the resulting diazonium compound with vinylidene chloride in the second step, and then reacting the trichloro- or bromodichloroethyl compound thus obtained with water or alcohols in the third step to give the arylacetic acid or esters thereof (see, for example, V M. Naidan and A. V Dombrovskii, *Zhurnal Obshchei Khimii* 34 (1984) 1469-73; EP-A-835243). This reaction, however, generally affords good yields only with those anilines which bear electron-withdrawing radicals on the aromatic and in which the amino group is not sterically blocked.

Additionally known is the reaction of bromobenzenes with chloroacetic acid derivatives in the presence of stoichiometric amounts of silver or copper at 180-200° C. Disadvantages of this process are the high temperature, which rules out use in the case of thermally sensitive compounds, the low yield and the use of stoichiometric amounts of metals which are costly and difficult to work up.

The reaction of aryl-Grignard compounds with α-haloacetic acid derivatives likewise leads to phenylacetic acid derivatives. A disadvantage, however, is the extremely limited tolerance of functional groups, which results from the use of highly reactive Grignard compounds which are difficult to handle.

Alternatives to the processes mentioned which have also been described are cross-couplings of aryl halides with Reformatsky reagents, tin enolates, copper enolates and other enolates, or ketene acetals (see, for example, *J. Am. Chem. Soc.* 1959, 81, 1627-1630; *J. Organomet. Chem.* 1979, 177, 273-281; *Synth. Comm.* 1987, 17, 1389-1402; *Bull. Chem. Soc. Jpn.* 1985, 58, 3383-3384; *J. Org. Chem.* 1993, 58, 7606-7607; *J. Chem. Soc. Perkin* 1 1993, 2433-2440; *J. Am. Chem. Soc.* 1975, 97, 2507-2517; *J. Am. Chem. Soc.* 1977, 99, 4833-4835; *J. Am. Chem. Soc.* 1999, 121, 1473-78; *J. Org. Chem.* 1991, 56, 261-263, *Heterocycles* 1993, 36, 2509-2512, *Tetrahedron Lett.* 1998, 39, 8807-8810). However, the applicability of these processes is limited. For instance, Reformatsky reagents and ketene acetals are difficult to prepare and handle. The use of tin compounds is disadvantageous for toxicological reasons, and the use of stoichiometric amounts of copper causes considerable costs in disposal. The use of enolates is generally possible only when no further enolizable groups are present in the molecule. For example, ketones are therefore ruled out as substrates for such processes. Some electrochemical processes are likewise known (*Synthesis* 1990, 369-381; *J. Org. Chem.* 1996, 61, 1748-1755), but these processes are disadvantageous due to the complex reaction regime and the low space-time yields.

Likewise already known is a method for preparing phenylacetic acid derivatives by a palladium-catalysed coupling reaction between arylboronic acids and ethyl bromoacetate (*Chem. Commun.* 2001, 660-70; DE-A-10111262). However, this process requires the preparation of the boronic acids, typically from the corresponding aryl or heteroaryl halides. Moreover, it has not been possible to date to use this preparation of sterically demanding, for example 2,6-disubstituted, phenylacetic acid derivatives. *Chem. Commun.* 2001, 660-70 states that sterically hindered arylboronic acids can also be converted efficiently under the conditions described therein. However, the examples contain only 2-tolylboronic acid as a sterically hindered substrate. Arylboronic acids with greater steric hindrance, for example 2,6-dialkylphenylboronic acids, are not described.

A further known method is that of the palladium- or copper-catalysed coupling reaction of aryl halides with malonic esters or β-keto esters, followed by a thermally induced dealkoxycarbonylation or retro-Claisen condensation. This involved reacting aryl iodides and activated aryl bromides with diethyl malonate in the presence of a palladium catalyst and 10 equivalents of very expensive caesium carbonate, and reaction times of up to 76 hours were needed (*Chem. Commun.* 2001, 2704-2705). Higher yields with shorter reaction times are possible, but these require the use of very specific N-heterocyclic carbene ligands which can be prepared only with difficulty; in addition, the expensive caesium carbonate is used here too (*Tetrahedron Lett.* 2004, 45, 5823-5825). The palladium- or copper-catalysed arylation of acetoacetic esters, followed by an in situ deacetylation, ultimately only has a narrow range of application; moreover, the deacetylation is frequently incomplete, which results in unsatisfactory yields of arylacetic esters (*Tetrahedron Lett.* 2004, 45, 4261-4264; *Tetrahedron Lett.* 2007, 48, 3289-3293).

All methods which have become known to date for preparing phenylacetic acid derivatives, more particularly also those with sterically demanding substitution, accordingly have shortcomings and disadvantages, some of them considerable, which complicate the use thereof. Since phenylacetic acids in general, and among them specifically also those with sterically demanding substitution, are important precursors, for example for active ingredients in crop protection, there is a need for a technically simple and highly efficient method for preparing such compounds.

SUMMARY

Surprisingly, a process for preparing aryl- and heteroarylacetic acids and derivatives thereof from aryl and heteroaryl halides and malonic esters has now been found, which is characterized in that the reaction is performed in the presence of a palladium catalyst, a phosphine, and A) an inorganic base and a phase transfer catalyst or B) a mixture of inorganic bases, the coupling reaction being followed by a dealkoxycarbonylation in situ.

DETAILED DESCRIPTION OF A PREFERRED EMBODIMENT

The discovery in process step A) that the addition of a phase transfer catalyst positively influences the selectivity of the reaction was unforeseeable and makes the discovery of this process particularly surprising. The use of the phase transfer catalyst makes it possible for the first time to shift selectivity and yield significantly in favour of the desired product. This makes the process much more economically viable than the processes known according to the prior art.

The discovery in process step B) that the use of a mixture of inorganic bases positively influences the conversion was unforeseeable and makes the discovery of this process particularly surprising. The use of a mixture of inorganic bases makes it possible for the first time to obtain the desired products in high selectivity and yield. This makes the process much more economically viable than the processes known according to the prior art.

The process according to the invention for preparing aryl- and heteroarylcarbonyl compounds is characterized in that aryl- or heteroaryl halides of the formula (I)

Ar-Hal  (I)

in which

Hal is chlorine, bromine or iodine and

Ar is the

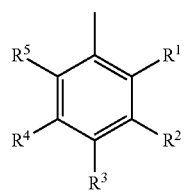

group, where $R^1$, $R^2$, $R^3$, $R^4$ and $R^5$ are the same or different and are each independently hydrogen, amino, cyano, nitro, halogen, optionally halogen-substituted $C_1$-$C_6$-alkyl, $C_1$-$C_6$-thioalkyl, thiophenyl, $C_1$-$C_6$-alkoxy, $C_6$-$C_{10}$-aryloxy, phenyl, —CO—$C_6$-$C_{10}$-aryl, —CO—$C_1$-$C_3$-alkyl, —COO—$C_1$-$C_6$-alkyl or —COO—$C_6$-$C_{10}$-aryl, the Ar radical may additionally also be a heteroaromatic radical such as 2-pyridyl, 3-pyridyl, 4-pyridyl, 2-furyl, 3-furyl, 2-thienyl or 3-thienyl or the Ar radical may also be 1- or 2-naphthyl, are reacted with malonic esters of the formula (II)

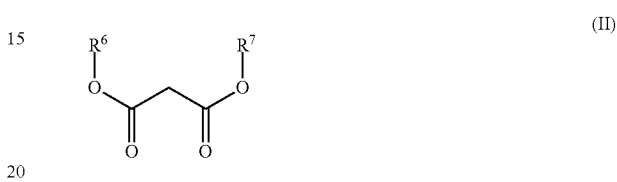

in which $R^6$ and $R^7$ are each independently optionally substituted $C_1$-$C_8$-alkyl, phenyl, aryl, or $NR^8R^9$, where $R^8$ and $R^9$ are the same or different and are each independently $C_1$-$C_4$-alkyl, or phenyl optionally substituted by optionally fluorine- or chlorine-substituted $C_1$-$C_3$-alkyl, by nitro, cyano or di-$C_1$-$C_3$-alkylamino, or together with the nitrogen atom to which they are bonded are a saturated or unsaturated, substituted or unsubstituted cycle, in the presence of a palladium catalyst, of a phosphine ligand and A) of an inorganic base and of a phase transfer catalyst or B) a mixture of inorganic bases, optionally using an organic solvent to give α-arylmethylcarbonyl compounds of the formula (III)

in which Ar and the $R^6$ and $R^7$ radicals are each as defined above.

This forms 2-arylmalonic diesters of the formula (IV) as intermediates, but they are not isolated.

This reaction is accordingly illustrated by the following reaction equation:

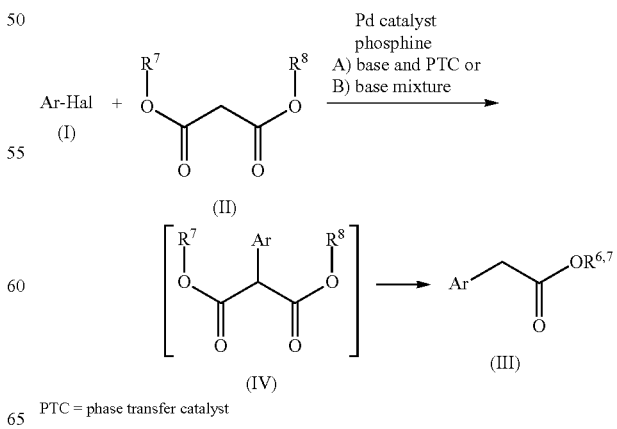

PTC = phase transfer catalyst

Preferred substituents or ranges of the radicals given in the formulae mentioned above and below are illustrated hereinafter:

Ar is preferably 1- or 2-naphthyl, 3-thienyl or the

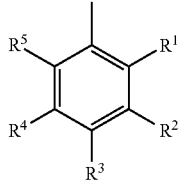

group, where
$R^1$, $R^2$, $R^3$, $R^4$ and $R^5$ are the same or different and are preferably each independently hydrogen, amino, cyano, nitro, fluorine, optionally fluorine-substituted $C_1$-$C_4$-alkyl, $C_1$-$C_4$-thioalkyl, thiophenyl, $C_1$-$C_4$-alkoxy, $C_6$-$C_{10}$-aryloxy, phenyl, —CO—$C_6$-$C_8$-aryl, —CO—$C_1$-$C_3$-alkyl, —COO—$C_1$-$C_4$-alkyl or —COO—$C_6$-$C_8$-aryl, Hal is preferably chlorine, bromine or iodine,
$R^6$ and $R^7$ are the same or different and are preferably each independently $C_1$-$C_4$-alkyl.

Ar is more preferably 1- or 2-naphthyl, 3-thienyl or the

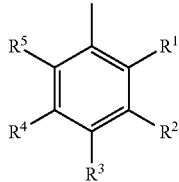

group, where
$R^1$, $R^2$, $R^3$, $R^4$ and $R^5$ are the same or different and are more preferably each independently hydrogen, amino, cyano, nitro, fluorine, methyl, methylthio, ethyl, i-propyl, n-propyl, $CF_3$, $C_2F_5$, $C_3F_7$, methoxy, ethoxy, phenyl, —CO-phenyl, —CO-methyl, —CO-ethyl, —COO-methyl, —COO-ethyl or —COO-phenyl, Hal is more preferably chlorine, bromine or iodine,
$R^6$ and $R^7$ are more preferably each independently methyl or ethyl, with emphasis for ethyl.

Ar is most preferably 1-naphthyl, 2-naphthyl, phenyl, 4-N,N-dimethylaminophenyl, 4-methylthiophenyl, 4-methoxyphenyl, 4-ethoxyphenyl, 3-methoxyphenyl, 2-methoxyphenyl, 2-methylphenyl, 3-methylphenyl, 4-methylphenyl, 4-fluorophenyl, 3-fluorophenyl, 2-fluorophenyl, 2-ethylphenyl, 4-ethoxycarbonylphenyl, 3-thienyl.

Ar is also most preferably 2,6-dimethylphenyl, 2,4,6-trimethylphenyl, 4-cyanophenyl, 4-cyano-2-methylphenyl, 3-cyanophenyl, 4-ethoxycarbonylphenyl, 4-trifluoromethylphenyl, 4-acetylphenyl, 4-nitrophenyl, 4-benzoylphenyl.

The abovementioned general or preferred radical definitions or illustrations can be combined with one another as desired, i.e. including combinations between the respective ranges and preferred ranges. They apply both to the end products and correspondingly to the intermediates.

The aryl halides of the formula (I) are known in principle or can be prepared by known methods.

The compounds of the formula (II) are known in principle or can be prepared by known methods.

The bases used in process step A) of the invention are inorganic bases such as alkali metal or alkaline earth metal hydroxides, carbonates, bicarbonates, oxides, phosphates, hydrogenphosphates, fluorides or hydrogenfluorides. Preference is given to using alkali metal and alkaline earth metal phosphates, carbonates or fluorides, and particular preference to using sodium phosphate and potassium phosphate. Emphasis is given to potassium phosphate.

The bases used in process step B) of the invention are mixtures of inorganic bases such as alkali metal or alkaline earth metal hydroxides, carbonates, bicarbonates, oxides, phosphates, hydrogenphosphates, fluorides or hydrogenfluorides, for example lithium hydroxide, sodium hydroxide, potassium hydroxide, caesium hydroxide, magnesium hydroxide, rubidium hydroxide, calcium hydroxide or barium hydroxide, lithium oxide, sodium oxide, potassium oxide, caesium oxide, magnesium oxide, rubidium oxide, calcium oxide or barium oxide, lithium phosphate, sodium phosphate, potassium phosphate, caesium phosphate, magnesium phosphate, rubidium phosphate, calcium phosphate or barium phosphate, lithium hydrogenphosphate, sodium hydrogenphosphate, potassium hydrogenphosphate, caesium hydrogenphosphate, magnesium hydrogenphosphate, rubidium hydrogenphosphate, calcium hydrogenphosphate or barium hydrogenphosphate, lithium fluoride, sodium fluoride, potassium fluoride, caesium fluoride, magnesium fluoride, rubidium fluoride, calcium fluoride or barium fluoride, lithium hydrogenfluoride, sodium hydrogenfluoride, potassium hydrogenfluoride, caesium hydrogenfluoride, magnesium hydrogenfluoride, rubidium hydrogenfluoride, calcium hydrogenfluoride or barium hydrogenfluoride, and lithium carbonate, sodium carbonate, potassium carbonate, magnesium carbonate, rubidium carbonate, calcium carbonate or barium carbonate, lithium bicarbonate, sodium bicarbonate, potassium bicarbonate, magnesium bicarbonate, rubidium bicarbonate, calcium bicarbonate or barium bicarbonate. Preference is given to using mixtures of alkali metal and alkaline earth metal phosphates, carbonates or bicarbonates, and particular preference to using mixtures of sodium carbonates and potassium carbonates and sodium bicarbonates and potassium bicarbonates. Emphasis is given to the mixture of potassium carbonate and potassium bicarbonate. The mixtures of the inorganic bases may contain different molar ratios of the individual bases. In general, molar ratios between 0.1 and 10 are used. Preference is given to working with molar ratios of 0.5 to 5.

In the process according to the invention, 1 to 10 equivalents of the respective base are used. Preference is given to using 1.2-5 equivalents of the base.

The palladium catalysts used in the process according to the invention are palladium(II) salts, for instance palladium chloride, bromide, iodide, acetate or acetylacetonate, which may optionally be stabilized by further ligands, for example alkyl nitriles, or Pd(0) species such as palladium on activated carbon, $Pd(PPh_3)_4$, bis(dibenzylideneacetone)palladium or tris(dibenzylideneacetone)dipalladium. Preference is given to bis(dibenzylideneacetone)palladium, tris(dibenzylideneacetone)dipalladium, palladium chloride, palladium bromide and palladium acetate; emphasis is given to bis(dibenzylideneacetone)palladium and palladium acetate.

The amount of palladium catalyst used in the process according to the invention is 0.001 to 5 mole percent, based on aryl halide used. Preferably, 0.005 to 3 mole percent is used, more preferably 0.01 to 1 mole percent.

The phosphine ligands used in the process according to the invention are $PR^{10}R^{11}R^{12}$ ligands where the $R^{10}$, $R^{11}$ and $R^{12}$ radicals are each hydrogen, linear and branched $C_1$-$C_8$-alkyl, vinyl, aryl or heteroaryl from the group of pyridine, pyrimidine, pyrrole, thiophene or furan, which may in turn be substituted by further substituents from the group of linear and branched $C_1$-$C_8$-alkyl or $C_6$-$C_{10}$-aryl, linear and branched $C_1$-$C_8$-alkyloxy or $C_1$-$C_{10}$-aryloxy, halogenated linear and branched $C_1$-$C_8$-alkyl or halogenated $C_6$-$C_{10}$-aryl, linear and branched $C_1$-$C_8$-alkyl or $C_6$-$C_{10}$-aryloxycarbonyl, linear and branched $C_1$-$C_8$-alkylamino, linear and branched $C_1$-$C_8$-dialkylamino, $C_1$-$C_8$-arylamino, $C_1$-$C_8$-diarylamino, formyl, hydroxyl, carboxyl, cyano, and halogens such as F, Cl, Br and I, obtained in situ.

Preferred phosphine ligands are trialkylphosphines such as triethylphosphine, tri-n-butylphosphine, tri-tert-butylphosphine, tricyclohexylphosphine, tris(1-adamantyl)phosphine, n-butyldi(1-adamantyl)phosphine (cataCXium® A), benzyldi(1-adamantyl)phosphine (cataCXium® ABn), 2-(di-tert-butylphosphino)biphenyl (JohnPhos), 2-(dicyclohexylphosphino)-2'-(N,N-dimethylamino)biphenyl (DavePhos) and 2-(dicyclohexylphosphino)-2',6'-dimethoxy-1,1'-biphenyl (SPhos). Particular preference is given to tri-tert-butylphosphine.

Tri-tert-butylphosphine can be used as the free phosphine or in the form of the $HBF_4$ adduct.

As an alternative to this, it is also possible to use defined palladium complexes which have been obtained from the abovementioned ligands in one or more process steps.

In the process according to the invention, 1-20 molar equivalents of phosphine are used, based on the amount of palladium used. Preferably, 1-4 molar equivalents are used.

In process step A) of the invention, a phase transfer catalyst from the group of the quaternary ammonium salts, the quaternary phosphonium salts or the crown ethers is used.

The phase transfer catalysts from the group of the quaternary ammonium salts or of the quaternary phosphonium salts preferably have the formula (V)

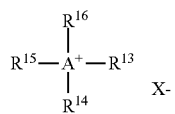

(V)

The $R^{13}$, $R^{14}$, $R^{15}$ and $R^{16}$ radicals are the same or different and are each independently $C_1$-$C_{28}$-alkyl, optionally branched $C_1$-$C_{28}$-alkyl, $C_6$-$C_{10}$-aryl, or benzyl.

A is N or P.

The X radical is halogen, hydrogensulphate, sulphate, dihydrogenphosphate, hydrogenphosphate, phosphate or acetate.

Preferably, X is bromine, chlorine, fluorine, hydrogensulphate, sulphate, phosphate and acetate.

Examples of such phase transfer catalysts include tetrabutylammonium fluoride, chloride, bromide, iodide and acetate, tetraethylammonium iodide, benzyltriethylammonium bromide, dodecyltrimethylammonium bromide and methyltridecylammonium chloride (Aliquat 336).

The phase transfer catalysts from the group of the crown ethers have the formula (VI)

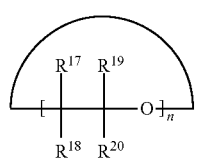

(VI)

in which n is a number from 4 to 8
and the
the $R^{17}$ to $R^{20}$ radicals are each independently hydrogen, $C_1$-$C_4$-alkyl or phenyl, where two adjacent R radicals may also in each case together form a cyclic radical such as cyclopentyl, cyclohexyl or 1,2-phenylene.

Examples of typical crown ethers of the formula (VI) include:

benzo-15-crown-5, 15-crown-5, 18-crown-6, dibenzo-18-crown-6, dibenzo-24-crown-8 and dicyclohexano-18-crown-6.

Preference is given to using 18-crown-6, dibenzo-18-crown-6 and dibenzo-24-crown-8.

Particular preference is given to 18-crown-6.

The amount of phase transfer catalyst in the process according to the invention is from 1 to 100 mole percent, based on aryl halide of the formula (I). Preference is given to amounts from 25 to 75 mole percent.

The process according to the invention is performed at temperatures of 0° C. to 220° C., preferably at 50° C. to 200° C. and more preferably at 100° C. to 180° C.

The process according to the invention can be performed in the presence of a solvent or using an excess of malonic ester of the formula (II). Preference is given to working in the presence of an excess of malonic ester of the formula (II).

The excess of malonic ester of the formula (II) is from 2 to 20 molar equivalents, based on the aryl halide of the formula (I). Preference is given to working with excesses of 3 to 10 molar equivalents.

The process according to the invention is typically performed at standard pressure, but can also be performed at reduced or elevated pressure.

To isolate the aryl- and heteroarylacetic acids and derivatives thereof prepared in accordance with the invention, the reaction mixture, after the reaction has ended, is worked up, preferably by distillation and/or by extraction or chromatographic methods.

The process according to the invention is illustrated by the examples which follow, without being restricted thereto.

PREPARATION EXAMPLES

Example 1 ethyl 4-methylphenylacetate

A dry Schlenk vessel was initially charged with 171 mg [1 mmol] of 4-bromotoluene, 1056 mg [6.6 mmol] of diethyl malonate, 2.88 mg [0.005 mmol] of $Pd(dba)_2$, 3.19 mg [0.011 mmol] of $P(tert-Bu)_3 \times HBF_4$, 594 mg [2.8 mmol] of dried $K_3PO_4$ and 132 mg [0.5 mmol] of 18-crown-6. The reaction vessel was three times evacuated and filled with nitrogen. This was followed by stirring at 160° C. until completion of conversion (8 to 12 hours). After cooling to room temperature, the reaction mixture was diluted with ethyl acetate. The resulting solution was washed successively with 20 ml each of water, saturated aq. $NaHCO_3$ solution and saturated aq. NaCl solution, dried over $MgSO_4$, filtered and concentrated under reduced pressure. Chromatographic purification using silica gel (hexane/ethyl acetate) gave ethyl 4-methylphenylacetate in a yield of 88% of theory.

$^1$H NMR (400 MHz, $CDCl_3$): δ=7.19 (d, J=8.0 Hz, 2H), 7.14 (d, J=8.0 Hz, 2H), 4.16 (q, J=8.0 Hz, 2H), 3.58 (s, 2H), 2.34 (s, 3H), 1.26 (t, J=8.0 Hz, 3H). $^{13}$C NMR (101 MHz, $CDCl_3$): δ=171.8, 136.6, 131.1, 129.2, 129.1, 60.8, 41.0, 21.0, 14.2. MS (70 eV), m/z (%): 178 (34) [M+], 106 (10), 105

(100). IR (NaCl): ṽ=2980 (vs), 2927 (m), 1735 (vs), 1515 (m), 1446 (m), 1367 (m), 1301 (m), 1253 (m), 1152 (m), 1032 (m), 809 (m).

Example 2 ethyl 2-ethylphenylacetate

Analogously to Example 1, 185 mg [1 mmol] of 2-ethylbromobenzene were used to obtain 170 mg of the title compound (88% of theory).

$^1$H NMR (400 MHz, CDCl$_3$): δ=7.27-7.16 (m, 4H), 7.56 (t, J=8.0 Hz, 1H), 7.46 (t, J=8.0 Hz, 2H), 7.39 (d, J=8.0 Hz, 2H), 4.17 (q, J=8.0 Hz, 2H), 3.68 (s, 2H), 2.70 (q, J=8.0 Hz, 2H), 1.29-1.23 (m, 6H). $^{13}$C NMR (101 MHz, CDCl$_3$): δ=171.6, 142.5, 132.0, 130.3, 128.4, 127.4, 125.9, 60.7, 38.5, 25.7, 14.8, 14.1. MS (70 eV), m/z (%): 193 (4), 192 (24) [M$^+$], 146 (29), 119 (100), 91 (54), 77 (21). IR (NaCl): ṽ=2980 (vs), 2935 (m), 1734 (vs), 1615 (m), 1583 (w), 1513 (s), 1246 (s), 1032 (m), 821 (m).

Example 3 ethyl 3-methoxyphenylacetate

Analogously to Example 1, 187 mg [1 mmol] of 3-bromoanisole were used to obtain 180 mg of the title compound (93% of theory).

$^1$H NMR (400 MHz, CDCl$_3$): δ=7.25 (t, J=8.0 Hz, 1H), 6.91-6.81 (m, 3H), 4.17 (q, J=8.0 Hz, 2H), 3.81 (s, 3H), 3.60 (s, 2H), 1.27 (t, J=8.0 Hz, 3H). $^{13}$C NMR (101 MHz, CDCl$_3$): δ=171.4, 159.6, 135.5, 129.4, 121.5, 114.8, 112.5, 60.8, 55.1, 41.4, 14.1. MS (70 eV), m/z (%): 195 (7), 194 (50) [M$^+$], 121 (100), 91 (37), 78 (17), 77 (26). IR (NaCl): ṽ=2979 (vs), 1731 (vs), 1601 (s), 1586 (m), 1492 (m), 1368 (m), 1262 (m), 1031 (m), 870 (m), 773 (m).

Example 4 ethyl 4-methylthiophenylacetate

Analogously to Example 1, 203 mg [1 mmol] of 4-bromothioanisole were used to obtain 199 mg of the title compound (95% of theory).

$^1$H NMR (400 MHz, CDCl$_3$): δ=7.25-7.18 (m, 4H), 4.14 (q, J=8.0 Hz, 2H), 3.56 (s, 2H), 2.46 (s, 3H), 1.24 (t, J=8.0 Hz, 3H). $^{13}$C NMR (101 MHz, CDCl$_3$): δ=171.5, 137.1, 131.0, 129.7, 126.9, 60.7, 40.8, 16.0, 14.2. MS (70 eV), m/z (%): 211 (16), 210 (100) [M$^+$], 137 (88), 121 (9). IR (KBr): ṽ=1730 (vs), 1495 (m), 1469 (m), 1366 (m), 1225 (m), 1031 (m), 802 (s).

Example 5 ethyl 3-thienylacetate

Analogously to Example 1, 163 mg [1 mmol] of 3-bromothiophene were used to obtain 160 mg of the title compound (94% of theory).

$^1$H NMR (400 MHz, CDCl$_3$): δ=7.29-7.26 (m, 1H), 7.14 (s, 1H), 7.04 (d, J=8.0 Hz, 1H), 4.16 (q, J=8.0 Hz, 2H), 3.64 (s, 2H), 1.26 (t, J=8.0 Hz, 3H). $^{13}$C NMR (101 MHz, CDCl$_3$): δ=170.1, 133.7, 128.5, 125.6, 122.7, 60.9, 35.9, 14.1. MS (70 eV), m/z (%): 171 (10), 170 (58) [M$^+$], 98 (22), 97 (100). R (NaCl): ṽ=2979 (s), 2937 (m), 1733 (vs), 1464 (m), 1369 (m), 1259 (m), 1206 (m), 1155 (m), 1028 (m).

Example 6 ethyl 4-methylphenylacetate

Analogously to Example 1, 128 mg [1 mmol] of 4-chlorotoluene were used to obtain the title compound in a yield of 85% of theory.

Example 7 ethyl 4-methylphenylacetate

Analogously to Example 1, 218 mg [1 mmol] of 4-iodotoluene were used to obtain the title compound in a yield of 91% of theory.

Example 8 ethyl 2-naphthylacetate

Analogously to Example 1, 207 mg [1 mmol] of 2-bromonaphthalene were used to obtain 200 mg of the title compound (93% of theory).

$^1$H NMR (400 MHz, CDCl$_3$): δ=7.87-7.79 (m, 3H), 7.75 (s, 1H), 7.51-7.42 (m, 3H), 4.18 (q, J=8.0 Hz, 2H), 3.79 (s, 2H), 1.27 (t, J=8.0 Hz, 3H). $^{13}$C NMR (101 MHz, CDCl$_3$): δ=171.5, 133.4, 132.4, 131.6, 128.1, 127.9, 127.61, 127.58, 127.3, 126.0, 125.7, 60.9, 41.6, 14.2. MS (70 eV), m/z (%): 215 (10), 214 (57) [M$^+$], 141 (100), 115 (31). IR (NaCl): ṽ=2980 (vs), 2936 (m), 1734 (vs), 1601 (m), 1508 (m), 1368 (m), 1258 (m), 1159 (m), 1031 (s), 859 (m), 818 (m), 802 (m), 759 (m), 742 (m).

Example 9 ethyl 4-methylphenylacetate

A dry Schlenk vessel was initially charged with 171 mg [1 mmol] of 4-bromotoluene, 1056 mg [6.6 mmol] of diethyl malonate, 1.12 mg [0.005 mmol] of Pd(OAc)$_2$, 3.19 mg [0.011 mmol] of P(tert-Bu)$_3$×HBF$_4$, 594 mg [2.8 mmol] of dried K$_3$PO$_4$ and 132 mg [0.5 mmol] of 18-crown-6. The reaction vessel was three times evacuated and filled with nitrogen. This was followed by stirring at 160° C. until completion of conversion (8 to 12 hours). After cooling to room temperature, the reaction mixture was diluted with ethyl acetate. The resulting solution was washed successively with 20 ml each of water, saturated aq. NaHCO$_3$ solution and saturated aq. NaCl solution, dried over MgSO$_4$, filtered and concentrated under reduced pressure. Chromatographic purification using silica gel (hexane/ethyl acetate) gave ethyl 4-methylphenylacetate in a yield of 75% of theory.

Example 10 ethyl 4-methylphenylacetate

A dry Schlenk vessel was initially charged with 171 mg [1 mmol] of 4-bromotoluene, 1056 mg [6.6 mmol] of diethyl malonate, 2.88 mg [0.005 mmol] of Pd(dba)$_2$, 2.22 mg [0.011 mmol] of P(tert-Bu)$_3$, 594 mg [2.8 mmol] of dried K$_3$PO$_4$ and 132 mg [0.5 mmol] of 18-crown-6. The reaction vessel was three times evacuated and filled with nitrogen. This was followed by stirring at 160° C. until completion of conversion (8 to 12 hours). After cooling to room temperature, the reaction mixture was diluted with ethyl acetate. The resulting solution was washed successively with 20 ml each of water, saturated aq. NaHCO$_3$ solution and saturated aq. NaCl solution, dried over MgSO$_4$, filtered and concentrated under reduced pressure. Chromatographic purification using silica gel (hexane/ethyl acetate) gave ethyl 4-methylphenylacetate in a yield of 76% of theory.

Example 11 ethyl 2,6-dimethylphenylacetate

A dry Schlenk vessel was initially charged with 185 mg [1 mmol] of 2,6-dimethylbromobenzene, 1056 mg [6.6 mmol] of diethyl malonate, 2.88 mg [0.005 mmol] of Pd(dba)$_2$, 3.19 mg [0.011 mmol] of P(tert-Bu)$_3$×HBF$_4$, 207 mg [1.5 mmol] of dried K$_2$CO$_3$ and 150 mg [1.5 mmol] of KHCO$_3$. The reaction vessel was three times evacuated and filled with nitrogen. This was followed by stirring at 160° C. until completion of conversion (8 hours). After cooling to room temperature, the reaction mixture was diluted with ethyl acetate. The resulting solution was washed successively with 20 ml each of water, saturated aq. NaHCO$_3$ solution and saturated aqueous NaCl solution, dried over MgSO$_4$, filtered and concentrated under reduced pressure. Chromatographic purification using silica gel (hexane/ethyl acetate) gave ethyl 2,6-dimethylphenylacetate in a yield of 81% of theory.

$^1$H NMR (400 MHz, CDCl$_3$): δ=7.11-7.03 (m, 3H), 4.16 (q, J=8.0 Hz, 2H), 3.70 (s, 2H), 2.35 (s, 6H), 1.26 (t, J=8.0 Hz, 3H). $^{13}$C NMR (101 MHz, CDCl$_3$): δ=171.2, 137.1, 131.7, 128.0, 126.9, 60.6, 35.4, 20.2, 14.1. MS (70 eV), m/z (%): 193 (9), 192 (37) [M$^+$], 119 (100), 118 (51), 91 (27). IR (NaCl): $\tilde{\nu}$=2979 (vs), 1734 (vs), 1589 (m), 1472 (m), 1445 (m), 1327 (m), 1246 (m), 1152 (s), 1031 (s), 769 (m).

Example 12 ethyl 2,4,6-trimethylphenylacetate

Analogously to Example 11, 199 mg [1 mmol] of 2,4,6-trimethylbromobenzene were used to obtain 172 mg of the title compound (83% of theory).

$^1$H NMR (400 MHz, CDCl$_3$): δ=6.89 (s, 2H), 4.17 (q, J=8.0 Hz, 2H), 3.7 (s, 2H), 2.33 (s, 6H), 2.29 (s, 3H), 1.27 (t, J=8.0 Hz, 3H). $^{13}$C NMR (101 MHz, CDCl$_3$): δ=171.4, 136.9, 136.3, 128.8, 128.7, 60.6, 35.0, 20.8, 20.1, 14.1. MS (70 eV), m/z (%): 207 (7), 206 (42) [M$^+$], 133 (100), 132 (39), 117 (12), 105 (15), 91 (14). IR (NaCl): $\tilde{\nu}$=2977 (vs), 2919 (vs), 1734 (vs), 1613 (s), 1580 (m), 1485 (m), 1445 (m), 1157 (m), 1030 (s), 850 (s), 783 (m).

Example 13 ethyl 4-cyano-2-methylphenylacetate

Analogously to Example 11, 196 mg [1 mmol] of 4-bromo-3-methylbenzonitrile were used to obtain 190 mg of the title compound (93% of theory).

$^1$H NMR (400 MHz, CDCl$_3$): δ=7.49-7.41 (m, 2H), 7.28 (d, J=8.0 Hz, 1H), 4.14 (q, J=8.0 Hz, 2H), 3.65 (s, 2H), 2.33 (s, 3H), 1.23 (t, J=8.0 Hz, 3H). $^{13}$C NMR (101 MHz, CDCl$_3$): δ=170.1, 138.3, 133.6, 130.9, 129.8, 118.8, 111.1, 61.2, 39.2, 19.4, 14.1. MS (70 eV), m/z (%): 204 (9), 203 (29) [M$^+$], 157 (19), 131 (40), 130 (100), 129 (20), 104 (16), 103 (37), 102 (12), 77 (23). IR (NaCl): $\tilde{\nu}$=2981 (vs), 2935 (vs), 2229 (vs), 1731 (vs), 1607 (m), 1569 (m), 1499 (m), 1367 (s), 1334 (s), 1256 (s), 1234 (s), 1216 (s), 1174 (s), 1162 (s), 1030 (s), 886 (w), 838 (w), 808 (w), 788 (w). Anal. calcd. for C$_{12}$H$_{13}$NO$_2$: H, 6.45; C, 70.92; N, 6.89. found: H, 6.61; C, 79.63; N, 6.56.

Example 14 ethyl 4-benzoylphenylacetate

Analogously to Example 11, 261 mg [1 mmol] of 4-bromobenzophenone were used to obtain 255 mg of the title compound (95% of theory).

$^1$H NMR (400 MHz, CDCl$_3$): δ=7.77 (t, J=8.0 Hz, 4H), 7.56 (t, J=8.0 Hz, 1H), 7.46 (t, J=8.0 Hz, 2H), 7.39 (d, J=8.0 Hz, 2H), 4.16 (q, J=8.0 Hz, 2H), 3.68 (s, 2H), 1.25 (t, J=8.0 Hz, 3H). $^{13}$C NMR (101 MHz, CDCl$_3$): δ=196.2, 170.8, 138.8, 137.5, 136.3, 132.3, 130.3, 129.9, 129.2, 128.2, 61.1, 41.3, 14.1. MS (70 eV), m/z (%): 269 (25), 268 (99) [M$^+$], 196 (44), 195 (70), 192 (94), 168 (100), 105 (69), 89 (51), 77 (51). IR (KBr): $\tilde{\nu}$=2981 (vs), 2935 (m), 1734 (vs), 1654 (vs), 1607 (s), 1578 (m), 1446 (m), 1277 (m), 1150 (m), 1029 (m), 701 (s).

Example 15 ethyl 4-trifluoromethylphenylacetate

Analogously to Example 11, 223 mg [1 mmol] of 4-bromobenzotrifluoride were used to obtain 190 mg of the title compound (82% of theory).

$^1$H NMR (400 MHz, CDCl$_3$): δ=7.59 (d, J=8.0 Hz, 2H), 7.42 (d, J=8.0 Hz, 2H), 4.17 (q, J=8.0 Hz, 2H), 3.68 (s, 2H), 1.27 (t, J=8.0 Hz, 3H). $^{19}$F NMR (376 MHz, CDCl$_3$): δ=62.6 (s, Ar—F). $^{13}$C NMR (101 MHz, CDCl$_3$): δ=170.7, 138.1, 129.6, 129.4 (q, $^2J_{C-F}$=32.3 Hz), 125.4 (q, $^3J_{C-F}$=4.0 Hz), 124.1 (q, $^1J_{C-F}$=272.7 Hz), 61.1, 41.0, 14.0. MS (70 eV), m/z (%): 233 (7), 232 (5) [M$^+$], 213 (14), 204 (18), 160 (23), 159 (100). IR (KBr): $\tilde{\nu}$=2983 (vs), 2938 (s), 1735 (vs), 1619 (m), 1586 (w), 1420 (m), 1326 (vs), 1164 (s), 1124 (s), 1067 (s), 1020 (m), 823 (w).

Example 16 ethyl 4-trifluoromethylphenylacetate

Analogously to Example 15, 179 mg [1 mmol] of 4-chlorobenzotrifluoride were used to obtain 170 mg of the title compound (73% of theory).

Example 17 ethyl 4-acetylphenylacetate

Analogously to Example 11, 199 mg [1 mmol] of 4-bromoacetophenone were used to obtain 150 mg of the title compound (73% of theory).

$^1$H NMR (400 MHz, CDCl$_3$): δ=7.90 (d, J=8.0 Hz, 2H), 7.36 (d, J=8.0 Hz, 2H), 4.14 (q, J=8.0 Hz, 2H), 3.65 (s, 2H), 2.57 (s, 3H), 1.23 (t, J=8.0 Hz, 3H). $^{13}$C NMR (101 MHz, CDCl$_3$): δ=197.6, 170.7, 139.4, 135.9, 129.7, 128.5, 61.1, 41.3, 26.6, 14.1. MS (70 eV), m/z (%): 207 (10) [M$^+$], 191 (100), 163 (21), 133 (20), 118 (10), 105 (35), 89 (21). IR (KBr): $\tilde{\nu}$=1735 (vs), 1683 (s), 1607 (m), 1472 (m), 1368 (m), 1269 (m), 1110 (m), 1031 (m), 957 (w).

Example 18 ethyl 4-acetylphenylacetate

Analogously to Example 17, 155 mg [1 mmol] of 4-chloroacetophenone were used to obtain 180 mg of the title compound (87% of theory).

Example 19 ethyl 4-nitrophenylacetate

Analogously to Example 11, 158 mg [1 mmol] of 4-chloronitrobenzene were used to obtain 147 mg of the title compound (70% of theory).
$^1$H NMR (400 MHz, CDCl$_3$): δ=8.18 (d, J=8.0 Hz, 2H), 7.45 (d, J=8.0 Hz, 2H), 4.16 (q, J=8.0 Hz, 2H), 3.17 (s, 2H), 1.25 (t, J=8.0 Hz, 3H). $^{13}$C NMR (101 MHz, CDCl$_3$): δ=170.1, 147.1, 141.4, 130.2, 123.7, 61.4, 41.0, 14.1. MS (70 eV), m/z (%): 210 (29), 209 (20) [M$^+$], 137 (100), 136 (72), 107 (99), 106 (41), 91 (21), 89 (94), 78 (90). IR (KBr): ν̃=2984 (m), 1734 (vs), 1604 (m), 1521 (s), 1348 (m), 1223 (m), 1174 (m), 1030 (m), 859 (m), 807 (m), 718 (m).

Example 20 ethyl 4-ethoxycarbonylphenylacetate

Analogously to Example 11, 185 mg [1 mmol] of ethyl 4-chlorobenzoate were used to obtain 208 mg of the title compound (88% of theory).
$^1$H NMR (400 MHz, CDCl$_3$): δ=8.01 (d, J=8.0 Hz, 2H), 7.36 (d, J=8.0 Hz, 2H), 4.37 (q, J=8.0 Hz, 2H), 4.16 (q, J=8.0 Hz, 2H), 3.67 (s, 2H), 1.39 (t, J=8.0 Hz, 3H), 1.25 (t, J=8.0 Hz, 3H). $^{13}$C NMR (101 MHz, CDCl$_3$): δ=170.8, 166.3, 139.1, 129.7, 129.2, 61.0, 60.9, 41.3, 14.3, 14.1. MS (70 eV), m/z (%): 237 (15), 236 (5) [M$^+$], 208 (11), 191 (39), 180 (13), 163 (100), 149 (18), 136 (25), 135 (47), 119 (13), 118 (18), 107 (40), 91 (24), 90 (28), 89 (35), 77 (13). IR (NaCl): ν̃=2983 (vs), 2938 (m), 1735 (vs), 1718 (vs), 1612 (m), 1368 (m), 1277 (s), 1106 (m), 1032 (s).

The invention claimed is:

1. A process for preparing a compound of formula (III)

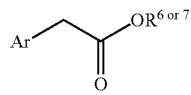

(III)

in which
Ar is a

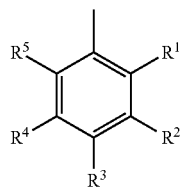

group,
where
R$^1$, R$^2$, R$^3$, R$^4$ and R$^5$ are the same or different and are each independently hydrogen, amino, cyano, nitro, halogen, optionally halogen-substituted C$_1$-C$_6$-alkyl, C$_1$-C$_6$-thioalkyl, thiophenyl, C$_1$-C$_6$-alkoxy, C$_6$-C$_{10}$-aryloxy, phenyl, —CO—C$_6$-C$_{10}$-aryl, —CO—C$_1$-C$_3$-alkyl, —COO—C$_1$-C$_6$-alkyl or —COO—C$_6$-C$_{10}$-aryl,
the Ar radical may additionally also be a heteroaromatic radical or
the Ar radical may also be 1- or 2-naphthyl,
and
R$^6$ and R$^7$ are each independently optionally substituted C$_1$-C$_8$-alkyl, phenyl, aryl, or NR$^8$R$^9$,
where R$^8$ and R$^9$ are the same or different and are each independently C$_1$-C$_4$-alkyl, or phenyl optionally substituted by optionally fluorine- or chlorine-substituted C$_1$-C$_3$-alkyl, by nitro, cyano or di-C$_1$-C$_3$-alkylamino, or together with the nitrogen atom to which they are bonded are a saturated or unsaturated, substituted or unsubstituted cycle,
wherein an aryl or heteroaryl halide of formula (I)

Ar-Hal (I)

in which
Hal is chlorine, bromine or iodine and
Ar is as defined above,
is reacted with a malonic ester of formula (II)

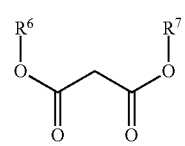

(II)

in the presence of a palladium catalyst, of a phosphine ligand and of a mixture of inorganic bases, without using caesium carbonate or caesium bicarbonate, wherein the mixture of inorganic bases comprises potassium carbonate and potassium bicarbonate in a ratio of 1:1,
optionally using an organic solvent.

2. The process for preparing a compound of formula (III) according to claim 1, where
Ar is 1- or 2-naphthyl, 3-thienyl or a

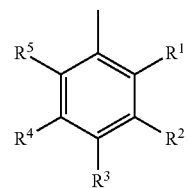

group,
where
R$^1$, R$^2$, R$^3$, R$^4$ and R$^5$ are the same or different and are each independently hydrogen, amino, cyano, nitro, fluorine, optionally fluorine-substituted C$_1$-C$_4$-alkyl, C$_1$-C$_4$-thioalkyl, thiophenyl, C$_1$-C$_4$-alkoxy, C$_6$-C$_{10}$-aryloxy, phenyl, —CO—C$_6$-C$_8$-aryl, —CO—C$_1$-C$_3$-alkyl, —COO—C$_1$-C$_4$-alkyl or —COO—C$_6$-C$_8$-aryl,
Hal is chlorine, bromine or iodine,
R$^6$ and R$^7$ are the same or different and are each independently C$_1$-C$_4$-alkyl.

3. The process for preparing a compound of formula (III) according to claim 1, where Ar is 1- or 2-naphthyl, 3-thienyl or a

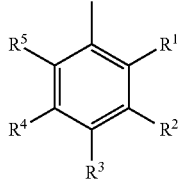

group,
where
R¹, R², R³, R⁴ and R⁵ are the same or different and are each independently hydrogen, amino, cyano, nitro, fluorine, methyl, methylthio, ethyl, i-propyl, n-propyl, $CF_3$, $C_2F_5$, $C_3F_7$, methoxy, ethoxy, phenyl, —CO-phenyl, —CO-methyl, —CO-ethyl, —COO-methyl, —COO-ethyl or —COO-phenyl, Hal is chlorine, bromine or iodine, R⁶ and R⁷ are each independently methyl or ethyl.

4. The process for preparing a compound of formula (III) according to claim 1, where
Ar is 1-naphthyl, 2-naphthyl, phenyl, 4-N,N-dimethylaminophenyl, 4-methylthiophenyl, 4-methoxyphenyl, 4-ethoxyphenyl, 3-methoxyphenyl, 2-methoxyphenyl, 2-methylphenyl, 3-methylphenyl, 4-methylphenyl, 4-fluorophenyl, 3-fluorophenyl, 2-fluorophenyl, 2-ethylphenyl, 4-ethoxycarbonylphenyl, 3-thienyl.

5. The process for preparing a compound of formula (III) according to claim 1, where
Ar is 2,6-dimethylphenyl, 2,4,6-trimethylphenyl, 4-cyanophenyl, 4-cyano-2-methylphenyl, 3-cyanophenyl, 4-ethoxycarbonylphenyl, 4-trifluoromethylphenyl, 4-acetylphenyl, 4-nitrophenyl, 4-benzoylphenyl.

6. The process for preparing a compound of formula (III) according to claim 1, where
R⁶ and R⁷ are each ethyl.

7. The process for preparing a compound of formula (III) according to claim 1, wherein the palladium catalyst used is bis(dibenzylideneacetone)palladium, tris(dibenzylideneacetone)dipalladium or palladium acetate.

8. The process for preparing a compound of formula (III) according to claim 1, wherein the phosphine ligand used is tri-tert-butylphosphine, tricyclohexylphosphine, tris(1-adamantyl)phosphine, n-butyldi(1-adamantyl)phosphine, benzyldi(1-adamantyl)phosphine, 2-(di-tert-butylphosphino)biphenyl or 2-(dicyclohexylphosphino)-2'-(N,N-dimethylamino.

9. The process for preparing a compound of formula (III) according to claim 1, wherein the phosphine ligand used is tri(tert-butyl)phosphine.

10. The process for preparing a compound of formula (III) according to claim 1, wherein a malonic ester of formula (II) is used as a solvent in excess.

11. The process for preparing a compound of formula (III) according to claim 1, wherein a temperature of from 100 to 180° C. is employed.

12. The process for preparing a compound of formula (III) according to claim 1, where Ar is a

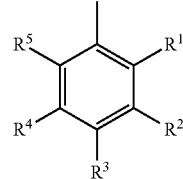

group,
where
R¹, R², R³, R⁴ and R⁵ are the same or different and are each independently hydrogen, amino, cyano, nitro, halogen, optionally halogen-substituted $C_1$-$C_6$-alkyl, $C_1$-$C_6$-thioalkyl, thiophenyl, $C_1$-$C_6$-alkoxy, $C_6$-$C_{10}$-aryloxy, phenyl, —CO—$C_6$-$C_{10}$-aryl, —CO—$C_1$-$C_3$-alkyl, —COO—$C_1$-$C_6$-alkyl or —COO—$C_6$-$C_{10}$-aryl.

* * * * *